United States Patent [19]
Eiden et al.

[11] 3,978,081

[45] Aug. 31, 1976

[54] 11H,12H-[1]BENZOPYRANO[2,3-b][1]BENZOPYRAN-11,12-DIONE AND DERIVATIVES

[75] Inventors: Fritz Eiden; Hans-Dieter Schweiger, both of Munich, Germany

[73] Assignee: Chem. pharmaz. Fabrik Dr. Hermann Thiemann GmbH, Lunen, Germany

[22] Filed: Mar. 12, 1975

[21] Appl. No.: 557,832

[30] Foreign Application Priority Data
Mar. 15, 1974 Germany............................ 2412582

[52] U.S. Cl. .......................... 424/275; 260/327 TH; 260/340.5; 260/345.2; 260/470; 260/473 G; 424/282; 424/283; 260/590 D
[51] Int. Cl.² ....................................... C07D 335/06
[58] Field of Search ....... 260/327 TH, 345.2, 340.5; 424/275, 282, 283

[56] References Cited
UNITED STATES PATENTS

| | | | |
|---|---|---|---|
| 3,752,830 | 8/1973 | von Strandtmann | 260/345.2 |
| 3,842,085 | 10/1974 | von Strandtmann | 260/289 R |

*Primary Examiner*—Natalie Trousof
*Assistant Examiner*—C. M. S. Jaisle

[57] ABSTRACT

Benzopyrano-benzopyranes and the sulfur analogs thereof, benzothiopyranobenzothiopyranes, useful as medicinal agents. Compositions of matter including 11H,12H-[1]benzopyrano[2,3-b][1]benzopyran-11,12-dione or 11H,12H-[1]benzothiopyrano[2,3-b][1]benzothiopyran-11,12-dione, and derivatives thereof including acid addition salts.

10 Claims, No Drawings

11H,12H-[1]BENZOPYRANO[2,3-b][1]BENZOPYRAN-11,12-DIONE AND DERIVATIVES

The invention is concerned with new benzopyranobenzopyranes and the sulfur analogs thereof, benzothiopyranobenzothiopyranes which are useful as medicinal agents.

The present new compound are of the formula:

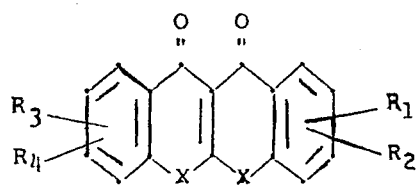

in which:

$R_1$, $R_2$, $R_3$ and $R_4$ are each hydrogen, trifluoromethyl, $C_1-C_{12}$ alkyl, $C_1-C_{12}$ alkoxy, halogen, or hydroxy, and $R_1$ and $R_2$ (or similarly $R_3$ and $R_4$) when taken together are methylenedioxy (—OCH$_2$O—)

X is sulfur or oxygen;

and salts thereof with acids, especially pharmaceutically acceptable acids such as the hydrohalic acids, perchloric acid and sulfuric acid monomethylester.

The radicals $R_1$–$R_4$ which are especially preferred include $C_1$–$C_4$ alkyl, particularly methyl, ethyl and propyl, $C_1$–$C_4$ alkoxy, particularly methoxyl, ethoxyl and propoxyl, chlorine and bromine, particularly chlorine, and trifluoromethyl.

In compounds where $R_1$ and $R_2$; and $R_3$ and $R_4$ are taken together as a methylenedioxy group, then it is preferred to have only one such group in the molecule.

According to the present invention, these compounds can be prepared by two different processes. In the first process, one coverts compounds of the following formula:

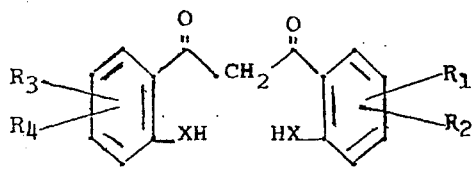

in a polar solvent system first with carbon disulfide and alkali hydroxide and then with an alkylating agent. Polar solvents for use in the reaction include, for example, dimethylsulfoxide or dimethylformamide; the alkali hydroxide includes sodium hydroxide or potassium hydroxide, and the alkylating agents include, for example, alkyl halides or dialkyl sulfates, especially those in which the alkyl group contains from 1 to 4 carbon atoms. For the alkylation reaction, the preferred agents are methyl iodide or dimethyl sulfate. This reaction is preferably conducted at a low temperature such as about 5°C. or less, for example, under ice cooling. The product may precipitate from the reaction mixture or alternatively water may be added to effect separation of the desired product. Either eventuality can be realised at the low temperatures employed for the reaction process.

The present new compounds can also be prepared in accordance with an alternate process in which compounds of the following formula:

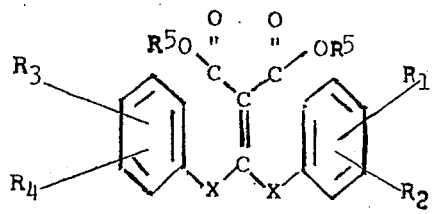

wherein $R_5$ is an alkyl radical, preferably a lower alkyl radical, are treated with polyphosphoric acid at elevated temperatures.

In this process, the temperature of the reaction can be in the range of 100°–150°C., preferably from about 125°–135°C. Polyphosphoric acid is a known compound and is prepared from orthophosphoric acid and phosphorus pentoxide, for example, from 2 parts of $H_3PO_4$ (85%) and 3 parts of $P_2O_5$.

The first of the two foregoing processes can be represented schematically as follows:

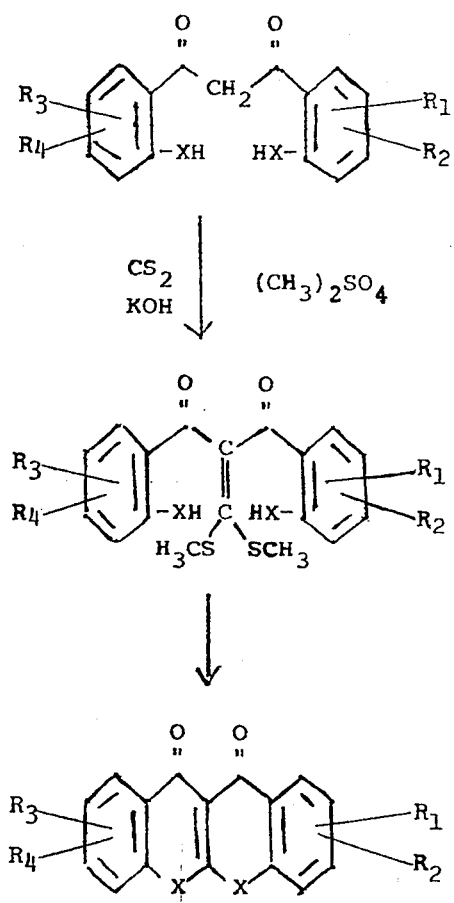

This reaction sequence is based upon the reaction of 2-hydroxy-2'-methoxy-bisbenzoylmethane with potassium hydroxide carbon disulfide and dimethyl sulfate yields 2-methylthio-3-(2'-methoxybenzoyl)-chromone (melting point 145°C) and the reaction of benzoyl-(2-methoxybenzoyl)-methane with potassium hydroxide carbon disulfide and dimethyl sulfate the compound 1-benzoyl-1-(2'-methoxybenzoyl)-2,2-dimethylthioethane (melting point 86°C.) is obtained.

The present new products form acid salts, for example salts with perchlorate acid, which are prepared by dissolving the present new compounds in acetic acid/acetic anhydride mixture (1:1) followed by addition of the perchloric acid in acetic acid. Especially preferred is 11H, 12H-[1] benzypyrano[2,3-b][1] benzopyran-11,12-dione.

The present new compounds are effective in heart and circulatory disorders and besides are useful in psychopharmacology and are useful in the treatment of asthma, spasms and thrombosis. The oral unit dosage will range from 50 to about 200 milligrams, e.g., 100 mg. while the daily oral dosage will range from 150 to about 600 milligrams, e.g., 300 mg.; the rectal unit dosage will range from 100 to 400 mg., e.g., 200 milligrams; the rectal daily dosage is 300 to 1200, e.g., 600 mg.; the parenteral unit dosage is 10 to 30 e.g., 20 mg. and the parenteral daily dosage is 20 to 100, e.g., 60 mg.

Tablets may be prepared, in which the active ingredient is finely pulverized and compounded with an inert extender such as, for example lactose, glucose, sucrose and starch as well as adsorption agents such as submicroscopic silicon dioxide, mixed with a lubricating agent such as talcum, magnesium stearate or microcrystalline cellulose. This mixture can either be pressed directly into tablets or first granulated with glucose syrup or an alcohol and then pressed.

Sugar coated pills may be prepared in the same manner as the tablets, by overcoating a base kernel with several adherent coatings of a sugary substance, and finally applying a wax layer. As the final layer one can also employ a coating resin such as combinations of cellulose acetate phthalate, polyethylene glycol, castor oil, sorbitan fatty acid ester, bees wax and other corollary materials.

Suppositories may be prepared, in which the active ingredient is homogeneously dispersed in a meltable suppository medium such as a triglyceride of a fatty acid and the resultant mixture poured out into suppositories.

For the production of capsules the active ingredient is finely ground with an inert extender such as lactose or sucrose and a flow control agent such as talcum, submicroscopic silicic acid or magnesium stearate, transformed into a flowable capsule-mass and then is poured into ordinary gelatin or starch capsules.

For the preparation of injections one dissolves the active ingredient either in pyrogen free water or in an organic solvation agent such as polyethylene glycol, polypropylene glycol, polyoxyethylene sorbitan fatty acid ester, with or without a supplementary preservative such as benzyl alcohol, p-hydroxybenzoic acid ester or phenylethanol. In certain cases one may dilute the organic solvent with a proportion of pyrogen free water. The solution may then be rendered isotonic with sodium chloride, made up to a physiologically acceptable pH level and microfiltered or sterilized.

The compounds according to this invention also serve as intermediates for the production of chromonocoumarins. By heating 11H, 12H-[1] benzopyrano[2,3-b][1]benzopyran-11,12-dion in acetic acid -water (2:1), the known compound 6H,7H-[1]benzyopyrano[4,3-b][1]-benzopyran-6, 7-dione (melting point 236°C) is obtained. (cf. M. Dean et al. J.C. 5 Perkin I, 1972, page 2007).

The preparation of the starting products of the first process is accomplished by reaction of 2-hydroxyacetophenone with methyl salicylate in the presence of sodium hydride, for example, in dry xylene.

The preparation of the starting material for the second process described herein is described in the dissertation of R. Kunz, Stuttgart 1964 (Methoden Organ. Chemie von Houben, Weyl und Muller, fourth edition Vol. II/4, page 444)

EXAMPLE I 11H,12H-[1]benzopyrano[2,3-b][1]benzopyran-11,12-dione

To a solution of 1,0 g. bis-(2-hydroxybenzoyl)-methane in 10.0 ml. Dimethylsulfoxide is added over 2 hours with cooling and stirring, 1.4 g. potassium hydroxide in 2.0 ml $H_2O$ and 2.0 ml. $CS_2$. Stirring is continued for 4 hours and 2.0 ml. dimethyl sulfate is then added at 5°C. The resulting precipitated, colorless product was recrystallized from acetone. Yield 0,5 g (47%); colorless needles m. 292°C.

$C_{16}H_8O_4$ (264.2) MS: m/e = 264 ($M^+$). IR (KBr): 1680cm$^{-1}$. NMR (DMSOD$_6$):$\delta$ =7.4 to 8.0 ppm (m,H$_{arom.}$); 8.0 to 8.3 ppm (m, H$_{arom.}$); Intensity 3:1.

The starting material was prepared as follows: 13.6 g. 2-hydroxyacetophenone and 19.2 g NaH in 200 ml. of dry xylene containing 2 drops of methanol were heated under reflux to boiling. Then 15.2 g of methyl salicylate were added and heating continued for 7 hours. The needlemass was washed with ether and ice-water/acetic acid (2:1) and then recrystallized from C Cl$_4$. Yield 5.0 g (20%); colorless crystals; m. 118°C.

$C_{15}H_{12}O_4$ (256.3) MS: m/e = 256 ($M^+$)

EXAMPLE 2

11H,12H-[1]benzothiopyrano[2,3-b][1]benzothiopyran-11,12-dione 3.6 g. methyl 3,3-bisphenylthio-2-carbomethoxy acrylate was heated in 30 g. polyphosphoric acid for 7 hours at 130°C. After cooling the mixture, 400 ml. of ice water was added, the mixture is filtered and the solid product recrystallized from acetone. Yield 1.1 g (36%); colorless crystals; m. 275°C.

$C_{16}H_8O_2S_2$ (296.4) MS: m/e = 296 ($M^+$) IR (KBr) 1658 cm$^{-1}$. NMR (CF$_3$COOD): $\delta$=8.0 to 8.3 ppm (m, H$_{arom.}$), 9.2 ppm (m, H$_{arom.}$); Intensity 3:1.

The starting product was obtained by the following procedure: To a solution of 1,1 g Na in 20 ml. absol. methanol, 5.0 g. thiophenol is added. After removal of the solvent under reduced pressure under $N_2$, 4.3 g. methyl 3,3-dichloro-2-carbomethoxy acrylate in 20 ml. ether is added portionwise. After 2 days, the solvent was removed under vacuum, the residue extracted with ether, and the ether extract was washed with water, dried and the solvent evaporated. The residue was column chromatographed (silica gel benzene). Yield 3.3 g. (46%); colorless plates; m. 50°C.

$C_{18}H_{16}O_4S_2$ (360,40) MS: m/e = 360 ($M^+$) IR (KBr): 1722,1700 cm$^{-1}$. NMR (CDCl$_3$): $\delta$=3,8 ppm (s, OCH$_3$), 7,0 to 7,3 ppm (H$_{arom.}$); Intensity 3:5.

In the same way, the following compounds were prepared:

11H,12H-[1]benzothiopyrano[2,3-b][1]benzothiopyran-2,9-dichlor-11,12-dione, m. 335°C; Yield 15%; $C_{16}H_6Cl_2O_2S_2$ (365.3) MS: m/e = 365 ($M^+$) IR (KBr): 1660 cm$^{-1}$. NMR (CF$_3$COOD): $\delta$ = 8,1 to 8,3 ppm (m,H$_{arom.}$); 9,2 ppm (m,H$_{arom.}$); Intensity 2:1.

11H,12H-[1]benzothiopyrano[2,3-b][1]benzothiopyran-2,9-dimethyl-11,12-dione, m. 238°C; Yield 21%; $C_{18}H_{12}O_2S_2$ (324,4) MS: m/e = 324 (M$^+$) IR (KBr): 1660 cm$^{-1}$; NMR (CF$_3$COOD): δ = 2,8 ppm (s, CH$_3$), 7,9 to 8,2 ppm (m,H$_{arom.}$), 9,1 ppm (m,H$_{arom.}$); Intensity 3:2:1.

EXAMPLE 3

Perchlorate salt of
11H,12H-[1]benzopyrano[2,3-b][1]benzopyran-11,12-dione and
11H,12H-[1]benzothiopyrano[2,3-b][1]benzothiopyran-11,12-dione 0.01 Mol 11H,12H-[1]benzopyrano[2,3-b][1] benzopyran-11,12-dione, and 11H,12H-[1]benzothiopyrano[2,3-b][1]benzothiopyrano-11,12-dione separately were dissolved in hot acetic acid/acetic anhydride (1:1) and 20 ml. 0.1 N HClO$_4$ acetic acid added. The precipitated salt was collected and washed with acetic acid. Yield: over 80%. Perchlorate of 11H,12H-[1]benzopyrano[2,3-b][1]benzopyran-11,12-dione: colorless needles; decomposed at ca. 240°C; $[C_{16}H_9O_4]_{ClO_4}$ (364.7): MS: m/e = 264 (M$^+$ — HClO$_4$) Perchlorate of 11H,12H-[1]benzothiopyrane[2,3-b][1]benzothipyran-11,12-dione: Yellow-green needles; decomposed at ca. 240°C. $[C_{16}H_9O_2S_2]ClO_4$ (396.8): MS: m/e = 296 (M$^+$ — HClO$_4$) IR (KBr): 3400,1655 cm$^{-1}$.

EXAMPLE 4

| Tablets | |
|---|---|
| 11H,12H-[1]benzopyrano[2,3-b]-[1]benzopyran-11,12-dione | 100 mg |
| Polyvinylpyrrolidone | 4 mg |
| Corn starch | 50 mg |
| Magnesium stearate | 10 mg |
| lactose | quantium satis |

The finely ground agent and lactose were ground with isopropanol and the granulate mixed with the remaining ingredients, after which the mass was pressed into tablets.

EXAMPLE 5

Sugar-coated tablets

The procedure of Example 4 is repeated and the pressed mass is then coated using usual processes.

EXAMPLE 6

| Suppositories | |
|---|---|
| 11H,12H-[1]benzothiopyrano[2,3-b]-[1]benzothiopyran-11,12-dione | 200 mg |
| Suppository base | 1800 mg |

The suppository base was melted at ca. 50°C. and the pulverized agent added (particle size 10–50 microns) to obtain 2 g. units.

EXAMPLE 7

| Capsules | |
|---|---|
| Product of Example 4 | 100 mg |
| lactose (particle size — 74 microns) | 100 mg |
| D-(+) Lactose | 50 mg |

The finely divided agent was mixed with the other ingredients and the mixture used to fill capsules.

EXAMPLE 8

| Injectable Composition | |
|---|---|
| Product of Example 4 | 20 mg |
| Polyethylene glycol | 750 mg |
| Isotonic NaCl solution | 3.0 ml |

The agent was dissolved in 25% aqueous polyethyleneglycol under warming (60°–80°C) with stirring and then the isotonic solution added after cooling. The ampules were then sterilized at 110°C or germ-filtered at room temperature.

WHAT WE CLAIM IS:
1. An 11H,12H-[1]benzopyrano[2,3-b][1]benzopyran-11,12-dione or an 11H,12H[1]benzothiopyrano[2,3-b][1]benzothiopyran-11,12 dione compound of the formula:

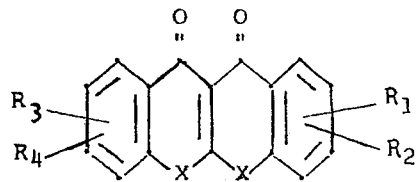

in which R$_1$, R$_2$, R$_3$ and R$_4$ are individually selected from the group consisting of hydrogen, trifluoromethyl, C$_1$–C$_{12}$ alkyl, C$_1$–C$_{12}$ alkoxy, halogen, or hydroxy; or R$_1$ and R$_2$; or R$_3$ and R$_4$ respectively comprise methylenedioxy; X is sulfur or oxygen; and an acid addition salt thereof.

2. The acid addition salt of claim 1, selected from the group consisting of hydrohalic acid, perchloric acid and sulfuric acid monomethyl ester salts.

3. 11H,12H-[1]benzopyrano[2,3-b][1]benzopyran-11,12-dione.

4. 11H,12H-[1]benzothiopyrano[2,3-b][1]benzothiopyran-11,12-dione.

5. 11H,12H[1]benzothiopyrano[2,3-b][1]benzothiopyran-2,9, dichlor-11,12-dione.

6. 11H,12H[1]benzothiopyrano[2,3-b][1]benzothiopyran-2,9, dimethyl-11,12-dione.

7. A medicinal agent for the treatment of asthma, spasms and thrombosis in unit dosage form comprising an effecting amount up to about 400 mg. of 11H,12H-[1]benzopyrano[2,3-b][1]benzopyran-11,12-dione and a pharmaceutically acceptable carrier.

8. A medicinal agent for the treatment of asthma, spasms and thombrosis in unit dosage form comprising an effective amount up to about 400 mg. of 11H,12H-[1]benzothiopyrano[2,3-b][1]benzothiopyrano-11,12-dione and a pharmaceutically acceptable carrier.

9. A medicinal agent for the treatment of asthma, spasms and thrombosis in unit dosage form comprising an effective amount up to about 400 mg. of 11H,12H-[1]benzothiopyrano[2,3-b][1] benzothiopyran-2,9, dichlor-11,12-dione and a pharmaceutically acceptable carrier 10. A medicinal agent for the treatment of asthma, spasms and thrombosis in unit dosage form comprising an effective amount up to about 400 mg. of 11H,12H[1]benzothiopyrano[2,3-b][1] benzothiopyran-2,9,dimethyl-11,12-dione and a pharmaceutically acceptable carrier.

* * * * *